US00PP26950P3

(12) United States Plant Patent

De Groot

(10) Patent No.: US PP26,950 P3

(45) Date of Patent: Jul. 19, 2016

(54) MINIATURE ROSE PLANT NAMED 'RUIPE0306B'

(50) Latin Name: *Rosa hybrida*
Varietal Denomination: RUIPE0306B

(71) Applicant: De Ruiter Intellectual Property B.V., Amstelveen (NL)

(72) Inventor: Hendrikus C. A. De Groot, Amstelveen (NL)

(73) Assignee: De Ruiter Intellectual Property B.V., Amstelveen (NL)

( * ) Notice: Subject to any disclaimer, the term of this patent is extended or adjusted under 35 U.S.C. 154(b) by 92 days.

(21) Appl. No.: 14/120,944

(22) Filed: Jul. 14, 2014

(65) Prior Publication Data

US 2015/0313048 P1 Oct. 29, 2015

(30) Foreign Application Priority Data

Apr. 28, 2014 (QZ) ..... PBR 2014/1149

(51) Int. Cl.
*A01H 5/02* (2006.01)

(52) U.S. Cl.
USPC ..... Plt./119

(58) Field of Classification Search
USPC ..... Plt./104, 105, 125, 126, 145, 146, 119, Plt./116
See application file for complete search history.

*Primary Examiner* — June Hwu

(74) *Attorney, Agent, or Firm* — Barbara Campbell; James M. Weatherly; Cochran Freund & Young LLC

(57) ABSTRACT

A new Rose plant particularly distinguished by having yellow-orange flowers and a mostly upright form, is disclosed.

2 Drawing Sheets

Genus and species: *Rosa hybrida.*
Denomination: 'RUIPE0306B'.

CROSS REFERENCE TO RELATED APPLICATIONS

This application claims, under 35 U.S.C. §119, priority to and the benefit of European Community Plant Variety Rights Application No. 2014/1149, filed Apr. 28, 2014, the entire contents of which are incorporated herein by reference for all purposes.

BACKGROUND

The present invention comprises a new and distinct variety of rose, botanically known as *Rosa* L., and hereinafter referred to by the variety name 'RUIPE0306B'. 'RUIPE0306B' originated from a cross conducted in May 2004 in Hazerswoude, The Netherlands between the proprietary female rose variety 'P-01-0152-001' (unpatented), and the proprietary male rose variety 'Ruira013a' (unpatented).

The seeds from the cross were sown and plants were grown in an unheated greenhouse for evaluation. An individual plant designated 'RUIPE0306B' was selected in January 2006. 'RUIPE0306B' was first vegetatively propagated in May 2006 in Hazerswoude, The Netherlands by branch cuttings. 'RUIPE0306B' was found to reproduce true to type in successive generations of asexual propagation via branch cuttings.

SUMMARY

The following are the most outstanding and distinguishing characteristics of this new variety when grown under normal horticultural practices in Amstelveen, The Netherlands.

1. 'RUIPE0306B' has a yellow-orange flower color; and
2. A mostly upright plant habit.

DESCRIPTION OF THE PHOTOGRAPHS

This new rose plant is illustrated by the accompanying photographs which show the plant's overall plant habit as well as various individual plant parts. The photograph is of 24-week-old plant taken indoors in Amstelveen, The Netherlands in January 2014. The colors shown are as true as can be reasonably obtained by conventional photographic procedures.

Figure 1:
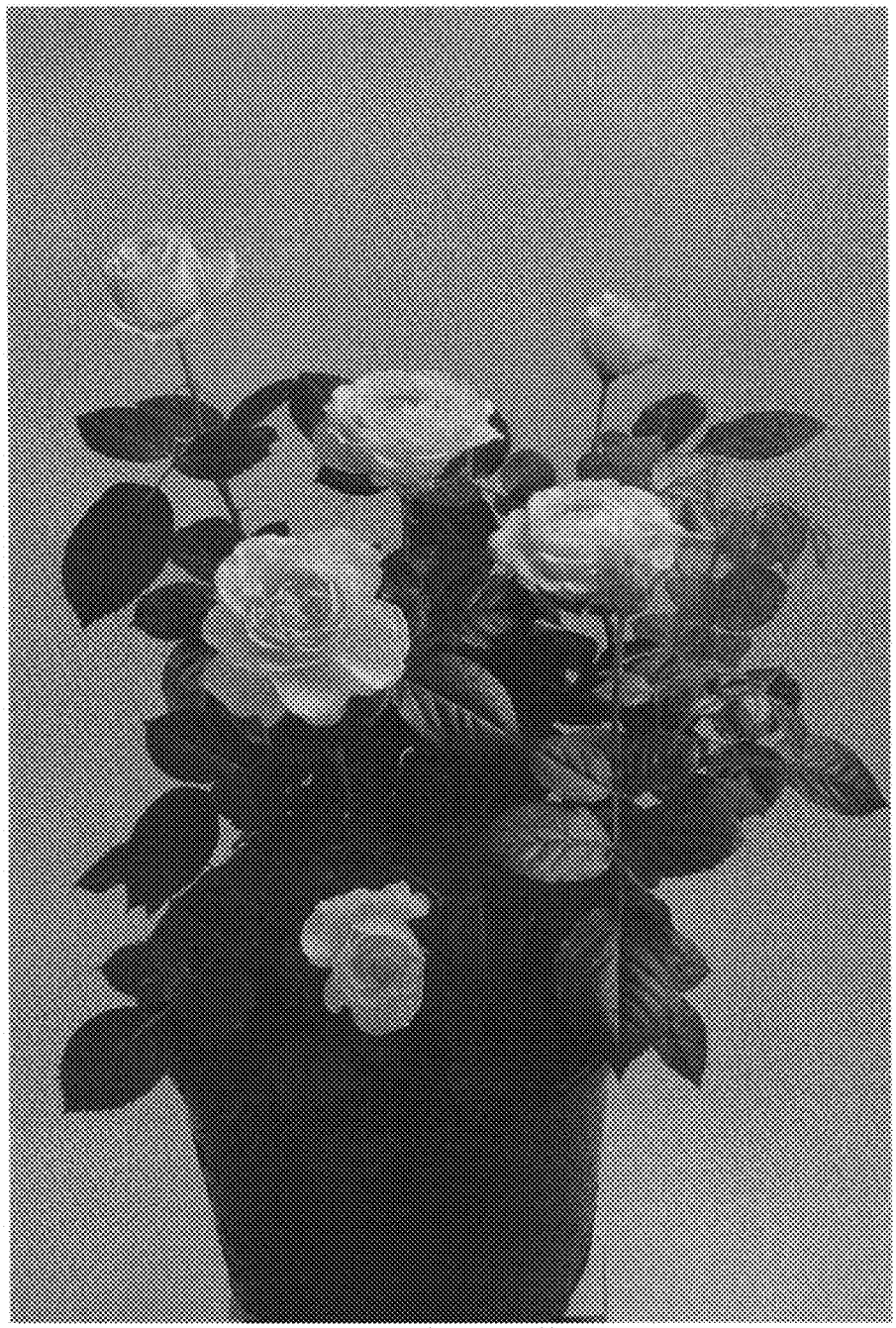
FIG. 1 shows the overall plant habit, including the blooms, buds, and foliage, in a pot.
Figure 2:
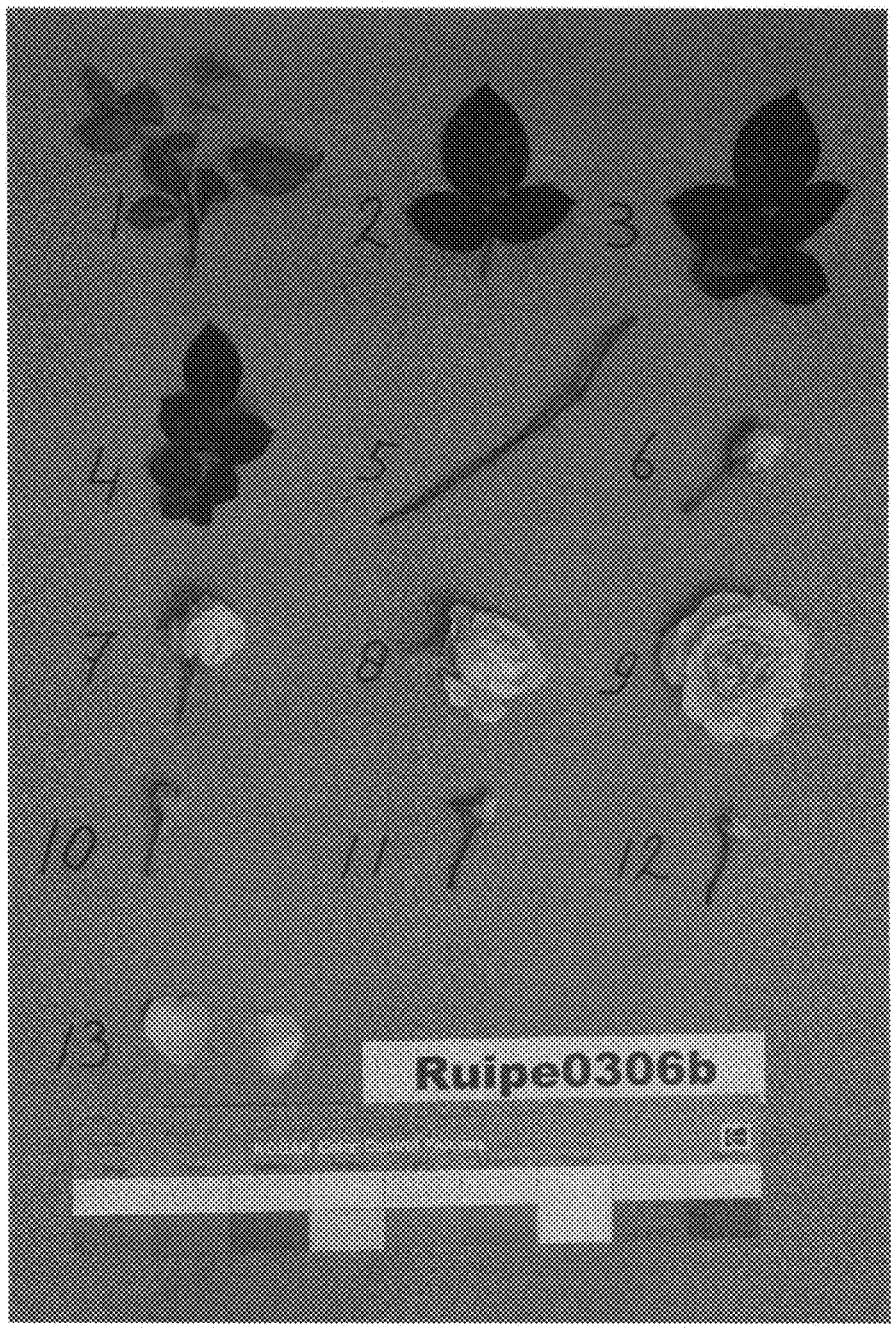
FIG.2 shows a close-up of individual flower parts of the plant, where.

1 shows immature leaves and leaflets.
2 shows a leaf having 3 leaflets.
3 shows a leaf having 5 leaflets.
4 shows a leaf having 7 leaflets.
5 shows a portion of a stem with thorns
6 shows a side view of a flower in immature bloom 6 weeks after sprouting.
7 shows a side view of a flower in immature bloom 4 weeks after sprouting.
8 shows a side view of a flower in immature bloom 4 weeks after sprouting.
9 shows a mature flower in bloom.
10 shows a side view of the sepals and reproductive organs after bloom.
11 shows a side view of the sepals and reproductive organs after bloom.
12 shows a side view of the reproductive organs without the sepals.
13 shows the upper and lower surfaces of individual petals.

DETAILED DESCRIPTION

The following detailed descriptions set forth the distinctive characteristics of 'RUIPE0306B'. The data which define these characteristics were collected from 24-week-old plants grown in a greenhouse without heating in Amstelveen, The Netherlands in January 2014. Color references are to The R.H.S. Colour Chart of The Royal Horticultural Society of London (R.H.S.), 1995.

Classification:

*Family*.—Rosaceae.

*Botanical*.—*Rosa* L.

*Designation*.—'RUIPE0306B'.

*Parentage*.—Female parent: The proprietary female rose variety 'P-01-0152-001' (unpatented). Male parent: The proprietary male rose variety 'Ruira013a' (unpatented).

Plant:

*Height*.—30.0 cm to 40.0 cm.

*Spread*.—25.0 cm.

*Form*.—Mostly upright.

*Time to produce a rooted cutting*.—Average 4 weeks.

*Time to bloom from propagation*.—Average 10 weeks.

*Lastingness of inflorescence on the plant*.—Average 3 weeks.

*Commercial classification*.—Miniature.

Lateral branches/peduncles:

*Color*.—RHS 138A.

*Pubescence*.—Absent.

*Stem shape*.—Rounded, glossy.

*Diameter*.—Average is 0.5 cm.

*Length*.—Average is 17.0 cm.

*Internode length*.—Average: 3.5 cm.

*Anthocyanin*.—Absent.

*Anthocyanin in young shoot*.—Present and weak.

*Thorns*.—Density (quantity per unit area): Average of 4 to 5 thorns per stem. Shape: Flat. Color: RHS 45B. Length: 0.7 cm. Width (at the base): Average of 0.2 cm.

Foliage:

*Arrangement*.—Compound, imparipinnate.

*Quantity of leaflets per leaf*.—3, 5, or 7 leaflets per leaf.

*Leaf length*.—Average: 10.0 cm.

*Leaf width*.—Average of 6.0 cm.

*Anthocyanin*.—Absent.

*Terminal leaflet*.—Length: 5.5 cm. Width: 2.5 cm to 3.0 cm. Shape: Ovate. Apex: Acuminate. Base: Round. Margin: Serrate. Color, immature leaf: Upper surface: RHS 143A. Lower surface: RHS 148B. Color, mature leaf: Upper surface: RHS 137A. Lower surface: RHS 137C. Texture, both upper and lower surfaces: Glabrous.

*Lateral leaflet*.—Length: Average of 0.4 cm. Width: Average of 2.5 cm. Shape: Ovate. Apex: Acuminate. Base: Round. Margin: Serrate. Color, immature leaf: Upper surface: RHS 143A. Lower surface: RHS 148B. Color, mature leaf: Upper surface: RHS 137A. Lower surface: RHS 137C. Texture, both upper and lower surfaces: Glabrous.

*Leaflet venation pattern*.—Pinnate.

*Leaflet venation color*.—Upper surface: RHS 138B. Lower surface: RHS 137C.

*Petiole of the leaf*.—Length: 0.7 cm. Diameter: 0.15 cm. Color: RHS 146B. Texture: Smooth. Thorns: Present, deep concave, 0.2 cm length.

*Petiole of the leaflet*.—Length: 0.15 cm. Diameter: 0.1 cm. Color: RHS 137C. Texture: Pubescent. Thorns: Absent.

*Stipules*.—Length: average: 0.8 cm. Width: average: 0.4 cm. Shape: Scale-like. Apex: Auricles about 0.5 cm length and 0.1 cm width. Base: Normal. Margin: Irregular protrusions. Color, immature leaf: Upper surface: RHS 146C. Lower surface: RHS 146B. Color, mature leaf: Upper surface: RHS 146B. Lower surface: RHS 146B. Texture, both upper and lower surfaces: Smooth.

Flowers or inflorescence:

*Appearance and arrangement*.—The flowers are born single on the peduncle, sometimes in a large spray with 3 flowers.

*Fragrance*.—Absent.

*Diameter*.—Average of 7.0 cm.

*Depth or height*.—Average of 3.0 cm.

*Lastingness of flowers on the plant*.—Average 14 to 16 days.

*Flower type*.—Double.

Buds:

*Length*.—Average of 2.4 cm.

*Width*.—Average of 1.8 cm.

*Shape*.—Ovate.

*Color*.—RHS 23C.

Petals:

*Quantity per flower*.—Average of 50 to 55 petals.

*Length*.—Average of 3.2 cm.

*Width*.—Average of 2.7 cm.

*Shape*.—Shell-shaped.

*Apex*.—One incision.

*Base*.—Cuneate.

*Margin*.—Reflexing.

*Color, when opening*.—Upper surface: RHS 9D and RHS 27D. Lower surface: RHS 9D and RHS 27D.

*Color, when fully open*.—Upper surface: RHS 9D and RHS 27D with a large inner petal basal spot, RHS 14C. Lower surface: RHS 9D and RHS 27D.

*Surface texture*.—Upper surface: Velvety. Lower surface: Velvety.

Petaloids: Absent.

Sepals:

*Quantity per flower*.—5.

*Length*.—2.5 cm.

*Width*.—1.0 cm.

*Extension*.—Absent.

*Shape*.—Ensiform.

*Apex*.—Acute, with a 1.0 cm long, thin point. Base: Truncate. Margin: Ciliate. Color: Upper surface: RHS 139C. Lower surface: RHS 137C.

*Surface texture*.—Upper surface: Pubescent. Lower surface: Pubescent.

Reproductive organs:

*Stamens*.—Quantity per flower: Average of 45. Anther color: RHS 22A. Anther shape: Bi-lobate. Filament length: 0.5 cm.

*Pistils*.—Quantity per flower: average: 50. Pistil length: average: 0.5 cm. Stigma shape: Fan-shaped. Stigma color: RHS 158C. Style length: average: 0.7 cm. Style color: RHS 158D. Receptacle: Height: 0.13 cm. Diameter: 0.15 cm. Color: RHS 144B. Texture: Smooth. Shape: Round globe.

Fruit and seed set: None observed to date.

Disease and pest/insect resistance: Mildew resistant, insects not observed.

COMPARISON WITH PARENTAL LINES AND KNOWN VARIETY

'RUIPE0306B' is a distinct variety of Rose and is distinguished from its parents as described in Table 1.

TABLE 1

Comparison with Parental Lines

| Characteristic | 'RUIPE0306B' | Female Parent 'P-01-0152-001' | Male Parent 'Ruira013a' |
|---|---|---|---|
| Flower color | Yellow-orange | Orange-red | Orange-pink |

When 'RUIPE0306B' is compared to the commercial variety 'RUIPE0306D', the following differences are described in Table 2.

TABLE 2

Comparison with Similar Variety

| Characteristic | 'RUIPE0306B' | 'RUIPE0306D' |
|---|---|---|
| Flower color | Yellow-orange | Orange-pink |
| Average number of petals per flower | 50 to 55 | 30 to 35 |

I claim:

1. A new and distinct variety of rose plant designated 'RUIPE0306B' as illustrated and described herein.

* * * * *